(12) United States Patent
Rabion et al.

(10) Patent No.: US 12,157,721 B2
(45) Date of Patent: Dec. 3, 2024

(54) PROCESS FOR THE PREPARATION OF METHYL 6-(2,4-DICHLOROPHENYL)-5-[4-[(3S)-1-(3-FLUOROPROPYL)PYRROLIDIN-3-YL]OXYPHENYL]-8,9-DIHYDRO-7H-BENZO[7]ANNULENE-2-CARBOXYLATE

(71) Applicant: Sanofi, Paris (FR)

(72) Inventors: Alain Rabion, Paris (FR); Michel Tabart, Paris (FR); Christian Wehrey, Paris (FR)

(73) Assignee: SANOFI, Paris (FR)

( * ) Notice: Subject to any disclaimer, the term of this patent is extended or adjusted under 35 U.S.C. 154(b) by 857 days.

(21) Appl. No.: 17/193,706

(22) Filed: Mar. 5, 2021

(65) Prior Publication Data

US 2021/0188771 A1    Jun. 24, 2021

Related U.S. Application Data

(63) Continuation of application No. PCT/EP2019/073827, filed on Sep. 6, 2019.

(30) Foreign Application Priority Data

Sep. 7, 2018    (EP) ..................... 18306177

(51) Int. Cl.
   *C07D 207/12*    (2006.01)
   *B01J 31/16*     (2006.01)
   *C07C 55/07*     (2006.01)
   *C07C 59/255*    (2006.01)

(52) U.S. Cl.
   CPC ........ *C07D 207/12* (2013.01); *B01J 31/1616* (2013.01); *C07C 55/07* (2013.01); *C07C 59/255* (2013.01)

(58) Field of Classification Search
   CPC .................................................. C07D 207/12
   See application file for complete search history.

(56) References Cited

U.S. PATENT DOCUMENTS

| | | |
|---|---|---|
| 6,495,607 B2 | 12/2002 | Bohlmann et al. |
| 7,429,681 B2 | 9/2008 | Pinney et al. |
| 7,612,114 B2 | 11/2009 | Hamaoka et al. |
| 7,799,824 B2 | 9/2010 | Lagu et al. |
| 8,299,112 B2 | 10/2012 | Smith et al. |
| 9,309,211 B2 | 4/2016 | Xiao et al. |
| 9,540,361 B2 | 1/2017 | Dijcks et al. |
| 9,714,221 B1 | 7/2017 | Bouaboula et al. |
| 9,845,291 B2 | 12/2017 | Liang et al. |
| 10,570,090 B2 | 2/2020 | Bouaboula et al. |
| 10,966,963 B2 | 4/2021 | Labadie et al. |
| 11,149,031 B2 | 10/2021 | Bouaboula et al. |
| 11,214,541 B2 | 1/2022 | Bouaboula et al. |
| 11,260,057 B2 | 3/2022 | Bouaboula et al. |
| 11,713,296 B2 | 8/2023 | Malpart et al. |
| 2012/0130219 A1 | 5/2012 | Zhao et al. |

(Continued)

FOREIGN PATENT DOCUMENTS

| | | |
|---|---|---|
| CN | 1309635 A | 8/2001 |
| CN | 106924210 A | 7/2017 |

(Continued)

OTHER PUBLICATIONS

Littke, A.F., et al., "Versatile Catalysts for the Suzuki Cross-Coupling of Arylboronic Acids with Aryl and Vinyl Halides and Triflates under Mild Conditions," Journal of the American Chemical Society, 122(17): 4020-4028 (2000).

(Continued)

*Primary Examiner* — Laura L Stockton
(74) *Attorney, Agent, or Firm* — McNeill PLLC

(57) ABSTRACT

Herein is provided a novel process for the preparation of methyl 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylate by a Suzuki coupling of compound (3), wherein LG represents a leaving group, with an organoboron reagent:

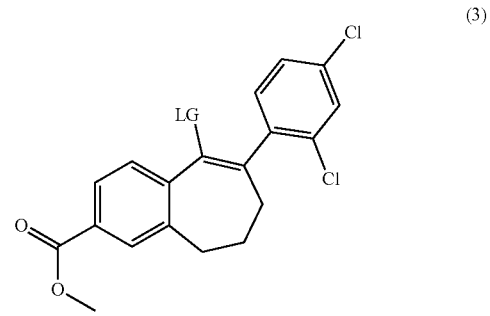

Compound (3) is obtained by activation of compound (4) with a leaving group LG, and compound (4) is obtained by alpha-arylation of methyl 5-oxo-6,7,8,9-tetrahydro-5H-benzo[7]annulene-2-carboxylate with 1-LG'-2,4-dichlorobenzene, wherein LG' represents a leaving group:

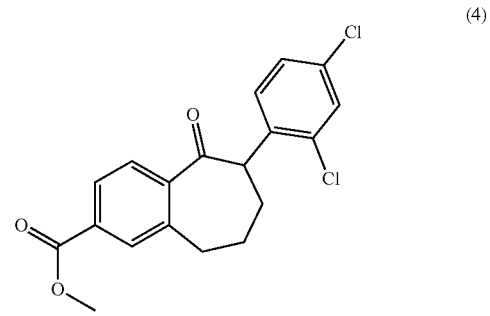

28 Claims, No Drawings

(56) References Cited

U.S. PATENT DOCUMENTS

| | | |
|---|---|---|
| 2013/0252890 A1 | 9/2013 | Wintermantel et al. |
| 2015/0080438 A1 | 3/2015 | Wintermantel et al. |
| 2015/0157606 A1 | 6/2015 | Maneval et al. |
| 2016/0184311 A1 | 6/2016 | Chen et al. |
| 2018/0153828 A1 | 6/2018 | Garner et al. |
| 2019/0167652 A1 | 6/2019 | Abrams et al. |
| 2020/0155521 A1 | 5/2020 | Schwartz et al. |
| 2020/0352905 A1 | 11/2020 | Cartot-Cotton et al. |
| 2020/0361918 A1 | 11/2020 | Bouaboula et al. |
| 2020/0392081 A1 | 12/2020 | Bouaboula et al. |
| 2021/0188771 A1 | 6/2021 | Rabion et al. |
| 2021/0188772 A1 | 6/2021 | Malpart et al. |
| 2022/0073460 A1 | 3/2022 | Bouaboula et al. |
| 2022/0204488 A1 | 6/2022 | Bouaboula et al. |
| 2022/0362248 A1 | 11/2022 | Bouaboula et al. |
| 2023/0028566 A1 | 1/2023 | Billot et al. |
| 2023/0089371 A1 | 3/2023 | Bouaboula et al. |
| 2023/0115865 A1 | 4/2023 | Boisnard et al. |
| 2023/0382854 A1 | 11/2023 | Bernardelli et al. |
| 2023/0404971 A1 | 12/2023 | Bouaboula et al. |
| 2024/0091194 A1 | 3/2024 | Cartot-Cotton et al. |
| 2024/0101512 A1 | 3/2024 | Bernardelli et al. |

FOREIGN PATENT DOCUMENTS

| | | |
|---|---|---|
| CN | 109896991 A | 6/2019 |
| EA | 023947 B1 | 7/2016 |
| EP | 1229036 A1 | 8/2002 |
| EP | 3434272 A1 | 1/2019 |
| JP | 2002520388 A | 7/2002 |
| JP | 2005528320 A | 9/2005 |
| JP | 2008512348 A | 4/2008 |
| JP | 2008546706 A | 12/2008 |
| JP | 2011500538 A | 1/2011 |
| JP | 2013530973 A | 8/2013 |
| JP | 2015500814 A | 1/2015 |
| WO | 1992015579 A1 | 9/1992 |
| WO | 2000/003979 A1 | 1/2000 |
| WO | 2003016270 A2 | 2/2003 |
| WO | 2003091239 A1 | 11/2003 |
| WO | 2004058682 A1 | 7/2004 |
| WO | 2006012135 A1 | 2/2006 |
| WO | 2006138427 A2 | 12/2006 |
| WO | 2009047343 A1 | 4/2009 |
| WO | 2009101634 A2 | 8/2009 |
| WO | 2012037410 A2 | 3/2012 |
| WO | 2012037411 A2 | 3/2012 |
| WO | 2012068284 A2 | 5/2012 |
| WO | 2013097773 A1 | 7/2013 |
| WO | 2015028409 A1 | 3/2015 |
| WO | 2016051374 A1 | 4/2016 |
| WO | 2016097071 A1 | 6/2016 |
| WO | 2016097072 A1 | 6/2016 |
| WO | 2016176666 A1 | 11/2016 |
| WO | 2017/140669 A1 | 8/2017 |
| WO | 2018/091153 A1 | 5/2018 |
| WO | 2019/020559 A1 | 1/2019 |
| WO | 2020049153 A1 | 3/2020 |
| WO | 2020112765 A1 | 6/2020 |
| WO | 2020225375 A1 | 11/2020 |
| WO | 2021116074 A1 | 6/2021 |
| WO | 2021170793 A1 | 9/2021 |
| WO | 2021178846 A1 | 9/2021 |
| WO | 2022084280 A1 | 4/2022 |
| WO | 2022084298 A1 | 4/2022 |
| WO | 2022106711 A1 | 5/2022 |
| WO | 2022218956 A1 | 10/2022 |
| WO | 2022218958 A1 | 10/2022 |

OTHER PUBLICATIONS

Billot, P. et al., Pending U.S. Appl. No. 17/783,364, filed Jun. 8, 2022.

Bouaboula, M., et al., Pending U.S. Appl. No. 17/802,223, filed Aug. 25, 2022.

El-Ahmad, Y., et al., "Discovery of 6-(2,4-Dichlorophenyl)-5-[4-[(3S)-1-(3-fluoropropyl)-pyrrolidin-3-yl]-oxyphenyl]-8,9-dihydro-7H-benzo[7]annulene-2-carboxylic acid (SAR439859), a Potent and Selective Estrogen Receptor Degrader (SERD) for the Treatment of Estrogen-Receptor-Positive Breast Cancer," Journal of Medicinal Chemistry, vol. 63, No. 2, pp. 512-528 (2019).

Gould, P., "Salt selection for basic drugs," International Journal of Pharmaceutics, vol. 33, pp. 201-217 (1986).

International Search Report for International Application No. PCT/EP2020/085011, mailed Jan. 25, 2021.

International Search Report for International Application No. PCT/EP2021/054815, mailed May 12, 2021.

Mannava, M.K.C., et al., "Enhanced Bioavailability in the Oxalate Salt of the Antituberculosis Drug Ethionamide," Crystal Growth & Design, vol. 16(3), pp. 1591-1598, (2016).

RN 1861739-57-2, Registry Database Compound, 2016.

Bouaboula, M., et al., Pending U.S. Appl. No. 17/579,187, filed Jan. 19, 2022.

Bernardelli, P., et al., Pending U.S. Appl. No. 18/032,500, filed Apr. 18, 2023.

Bernardelli, P., et al., Pending U.S. Appl. No. 18/032,502, filed Apr. 18, 2023.

International Search Report for International Application No. PCT/EP2021/078883, mailed Dec. 9, 2021.

International Search Report for International Application No. PCT/EP2021/078916, mailed Dec. 9, 2021.

Anonymous, "Phase 1 / 2 Study of Amcenestrant (SAR439859) Single Agent and in Combination With Other Anti-cancer Therapies in Postmenopausal Women With Estrogen Receptor Positive Advanced Breast Cancer," Sep. 15, 2017, URL: https://www.clinicaltrials.gov/ct2/show/NCT03284957.

Besret, et al., "Translational strategy using multiple nuclear imaging biomarkers to evaluate target engagement and early therapeutic efficacy of SAR439859, a novel selective estrogen receptor degrader", EJNMMI Research, Biomed Central Ltd, London, UK, vol. 10, No. 1, Jun. 29, 2020, pp. 1-13.

Bouaboula, M., et al., Pending U.S. Appl. No. 18/286,496, filed Oct. 11, 2023.

Bouaboula, M., et al., Pending U.S. Appl. No. 18/286,510, filed Oct. 11, 2023.

International Search Report for International Application No. PCT/EP2022/059700, mailed Jul. 8, 2022.

International Search Report for International Application No. PCT/EP2022/059704, mailed Jul. 21, 2022.

Robinson, Dan, R. et al., "Activating ESR1 mutations in hormone-resistant metastatic breast cancer", Nat. Genet., Dec. 2013, 45(12), 1446-1451.

Toy, Weiyi, et al., "Activating ESR1 mutations differentially impact the efficacy of ER antagonists", Cancer Discovery, Mar. 2017, 7(3), 277-287.

Bouaboula, M. et al., Pending U.S. Appl. No. 18/037,949, filed May 19, 2023.

Cancer [online]—Medline Plus, [Retrieved on Jul. 6, 2007] Retrieved from the Internet, URL: http://www.nlm.nih.gov/medlineplus/cancer.html, pp. 1-10.

Bardia, A., et al., Dose-escalation study of SAR439859, an oral selective estrogen receptor (ER) degrader (SERD), in postmenopausal women with ER+/HER2− metastatic breast cancer (mBC), Journal of Clinical Oncology, vol. 37, Suppl. 15, p. 1054 (May 20, 2019).

Campone, M., et al., "Abstract P5-11-02: Dose-escalation study of SAR439859, an oral selective estrogen receptor degrader, in postmenopausal women with estrogen receptor-positive and human epidermal growth factor receptor 2− negative metastatic breast cancer," Cancer Research, vol. 80, Suppl. 4, pp. 1-4 (Feb. 2020).

Extended European Search Report issued in European Application No. 19305593.6 on Oct. 30, 2019, 7 pages.

Franks, et al., "Selective Estrogen Receptor Modulators: Cannabinoid Receptor Inverse Agonists with Differential CB1 and CB2 Selectively," Frontiers inPharmacology, vol. 7, No. 503, pp. 1-16 (2016).

(56) References Cited

OTHER PUBLICATIONS

International Search Report for PCT/EP2020/062743, mailed Aug. 10, 2020.
Jordan, Craig V., "Antiestrogens and Selective Estrogen Receptor Modulators as Multifunctional Medicines. 1. Receptor Interactions," Journal of Medicinal Chemistry, vol. 46, No. 6, pp. 883-908 (2003).
Miller, Chris P., "SERMs: Evolutionary Chemistry, Revolutionary Biology," Current Pharmaceutical Design, vol. 8, No. 23, pp. 2089-2111 (2002).
Pending U.S. Appl. No. 16/870,031, inventors Sylvaine Cartot-Cotton et al., filed May 8, 2020.
Pending U.S. Appl. No. 17/193,706, inventors Alain Rabion et al., filed Mar. 5, 2021.
Pending U.S. Appl. No. 17/460,629, inventors Monsif Bouaboula et al., filed Aug. 30, 2021.
Pending U.S. Appl. No. 17/532,051, inventors Monsif Bouaboula et al., filed Nov. 22, 2021.
Pending U.S. Appl. No. 17/765,169, inventors Sabine Boisnard et al., filed Mar. 30, 2022.
Pickar, et al., "SERMs: Progress and future perspectives," Maturitas, Elsevier, vol. 67, pp. 129-138 (2010).
Ullrich, et al., "Estrogen receptor modulator review," Expert Opinion, vol. 16, No. 5, pp. 559-572 (2006).
Deroo, B.J., et al., "Estrogen Receptors and Human Disease", The Journal of Clinical Investigation, Mar. 2006, vol. 116, No. 3, pp. 561-570.
Golub et al., "Molecular Classification of Cancer: Class Discovery and Class Prediction by Gene Expression Monitoring", Science, Oct. 15, 1999, vol. 286, pp. 531-537.
International Search Report for International Application No. PCT/EP2017/053282, mailed Jul. 6, 2017.
International Search Report for International Application No. PCT/EP2017/068446, mailed Sep. 12, 2017.
International Search Report for International Application No. PCT/EP2018/069901, mailed Oct. 12, 2018.
Lala, P.K., et al., "Role of Nitric Oxide in Tumor Progression: Lessons From Experimental Tumors", Cancer Metastasis Reviews, Mar. 1998, vol. 17, No. 1, pp. 91-106.
Pending U.S. Appl. No. 16/414,558, filed May 16, 2019.
Pending U.S. Appl. No. 16/634,089, filed Jan. 24, 2020.
Pending U.S. Appl. No. 17/124,852, filed Dec. 17, 2020.
Ruff, et al., "Estrogen Receptor Transcription and Transactivation Structure-Function Relationship in DNA– and Ligand– Binding Domains of Estrogen Receptors", Breast Cancer Research, 2000, vol. 2, No. 5, pp. 353-359.
Translation of Office Action issued in Japanese Application No. 2018-515615, mailed on Sep. 18, 2018, 3 pages.
Translation of Search Report issued in Chinese Application No. 201780023008.0, mailed Apr. 23, 2020, 3 pages.
Anstead, Gregory M. et al., "2,3-Diarylindenes and 2,3-Diarylindenones: Synthesis, Molecular Structure, Photochemistry, Estrogen Receptor Binding Activity, and Comparisons with Related Triarylethylenes", J. Med.Chem., 1988, vol. 31, No. 7, pp. 1316-1326.
McCague, Raymond et al., "Nonisomerizable Analogues of (Z)– and (E)-4-Hydroxytamoxifen. Synthesis and Endocrinological Properties of Substituted Diphenylbenzocycloheptenes", J. Med.Chem., 1988, vol. 31, No. 7, pp. 1285-1290.
International Search Report for PCT/EP2019/073823, dated Oct. 10, 2019, 3 pages.
International Search Report for PCT/EP2019/073827, dated Oct. 9, 2019, 3 pages.
Pending U.S. Appl. No. 17/193,776, filed Mar. 5, 2021 (Not enclosed).
Chandarlapaty, S., et al., "277MO SAR439859, an oral selective estrogen receptor (ER) degrader (SERD), in ER+/ HER2– metastatic breast cancer (mBC): Biomarker analyses from a phase I/II study", Annals of Oncology, vol. 31, No. S4, Sep. 1, 2020, p. S351.
International Search Report for International Application No. PCT/EP2021/082583, mailed Feb. 25, 2022.

PROCESS FOR THE PREPARATION OF METHYL 6-(2,4-DICHLOROPHENYL)-5-[4-[(3S)-1-(3-FLUOROPROPYL) PYRROLIDIN-3-YL]OXYPHENYL]-8,9-DIHYDRO-7H-BENZO[7]ANNULENE-2-CARBOXYLATE

The present application is a continuation of International Application No. PCT/EP2019/073827, filed Sep. 6, 2019, which claims priority from European Patent Application No. 18306177.9, filed Sep. 7, 2018, each of which is incorporated by reference herein in its entirety for any purpose.

Herein is provided a novel process for the preparation of methyl 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylate, and novel compounds useful in such a process.

Methyl 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylate, also named as 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid methyl ester and hereafter designated as "compound (2)", is the N−1 intermediate in the synthesis of 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid (hereafter "compound (1)"). Indeed, compound (1) can be obtained by saponification of compound (2).

Compound (1), depicted below, is a selective estrogen receptor degrader (SERD) which has estrogen receptor antagonist properties and accelerates the proteasomal degradation of the estrogen receptor. It may be used in particular as anticancer agent. This compound is disclosed in the patent application WO 2017/140669.

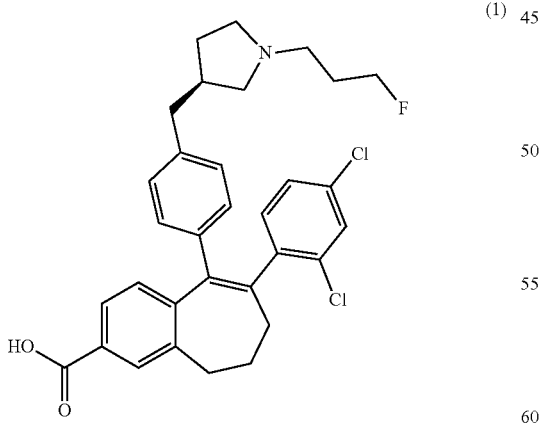
(1)

For active ingredients in medicinal products and their synthesis intermediates there is always a need to find new synthesis routes more adapted for industrial implementation.

Herein is described a novel process for the preparation of compound (2) (methyl ester of compound (1)):

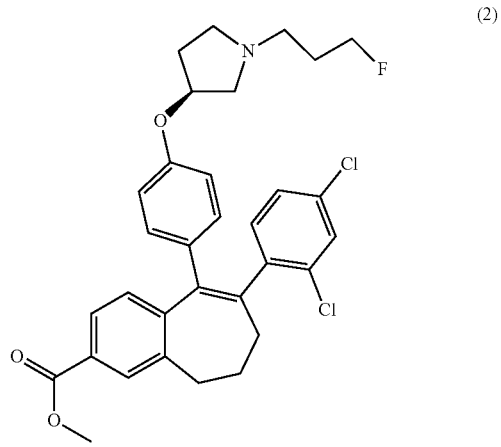
(2)

in the base form or in a salt form, characterized in that compound (2) is obtained by a Suzuki coupling of compound (3), wherein LG represents a leaving group, with an organoboron reagent:

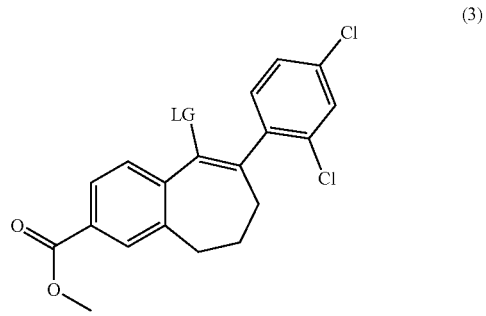
(3)

optionally followed by a salification reaction.

Herein is provided a process for the preparation of compound (2):

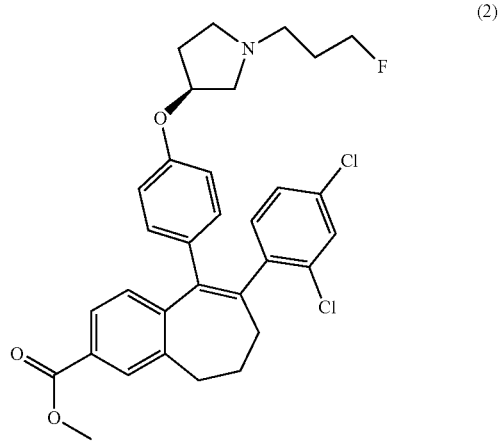 [SMILES: COC(=O)c1ccc2c(c1)CCCC(c1ccc(Cl)cc1Cl)=C2c1ccc(O[C@H]2CCN(CCCF)C2)cc1]
(2)

in the base form or in a salt form, characterized in that compound (2) is obtained by a Suzuki coupling of compound (3),

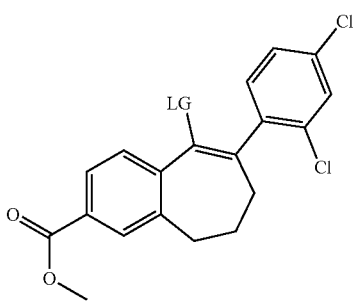

(3)

wherein LG represents a leaving group,
with an organoboron reagent OrganoB-X wherein OrganoB is a boron derivative and X is a (3S)-1-(3-fluoropropyl)-3-phenoxypyrrolidine moiety of the following formula:

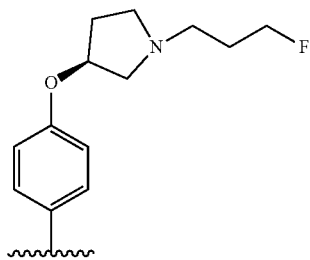 [SMILES: *c1ccc(O[C@H]2CCN(CCCF)C2)cc1]

optionally followed by a salification reaction.

In an embodiment of the process provided herein, compound (3) as described above is obtained by activation of compound (4) with a leaving group LG:

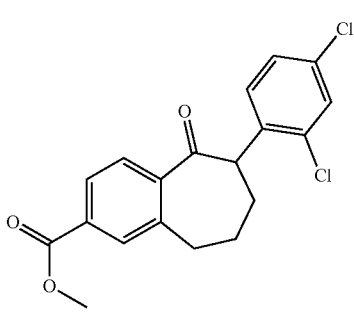

(4)

In another embodiment of the process provided herein, compound (4) as described above is obtained by alpha-arylation of methyl 5-oxo-6,7,8,9-tetrahydro-5H-benzo[7]annulene-2-carboxylate (represented as compound (5) below) with 1-LG'-2,4-dichlorobenzene as defined herein after:

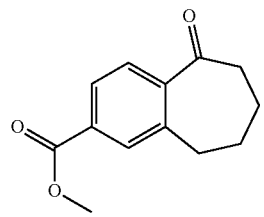

(5)

According to the present invention, LG' represents any leaving group.

In one embodiment, LG' represents
i. a leaving group of the formula —O—SO$_2$—C$_n$F$_{(2n+1)}$ with n=1 to 4, more particularly a triflate (wherein n=1) or a nonaflate (wherein n=4), or
ii. a halogen atom selected from bromine or iodine.

In one particular embodiment 1-LG'-2,4-dichlorobenzene is 1-Hal-2,4-dichlorobenzene, wherein Hal represents a halogen atom selected from bromine or iodine.

In the process provided herein, the leaving groups LG and LG' are defined as a chemical moiety displaying leaving group properties and allowing further substitution in a subsequent chemical reaction.

More particularly, the leaving group LG in compound (3) is obtained by activating the carbonyl function in compound (4). Conventional activation reactions of the carbonyl function in compound (4) may be used as known to one of skill in the Art.

For example, the leaving group LG in compound (3) may be a halogen atom or an alkyl or aryl sulfamate, an alkyl or aryl phosphate or an alkyl or aryl sulfonate, in particular a halogen atom or an alkyl or aryl sulfonate.

In an embodiment, the leaving group in compound (3) may be a halogen atom or a mesylate, tosylate, sulfamate, phosphate or triflate group.

In another embodiment of the present invention, the leaving group LG is a halogen atom or a mesylate, tosylate, sulfamate, phosphate, triflate or nonaflate group.

In a particular embodiment of the present invention, the leaving group LG is a triflate or a nonaflate group.

Advantageously, the leaving group LG is the triflate group (trifluoromethanesulfonyl, corresponding to the formula —O—S(O)$_2$—CF$_3$).

In the context of the present invention, the terms below have the following definitions unless otherwise mentioned throughout the instant specification:

an alkyl group: a linear or branched saturated hydrocarbon-based aliphatic group comprising, unless otherwise mentioned, from 1 to 6 carbon atoms (noted "(C$_1$-C$_6$)-alkyl"). By way of examples, mention may be made of, but not limited to: methyl, ethyl, propyl, n-propyl, isopropyl, butyl, isobutyl, sec-butyl, tert-butyl, pentyl, isopentyl, hexyl and isohexyl groups, and the like. Said groups may be partially or fully substituted by fluorine atoms and include but not be limited to perfluoromethyl, perfluoroethyl, perfluoropropyl, perfluorobutyl, and the like;

an aryl group: phenyl, naphtyl or substituted phenyl, wherein a substituted phenyl is defined as a phenyl group in which one or more of the hydrogens has been replaced by the same or different substituents including, but not limited to: halogen atom, alkyl, nitro, cyano, alkoxy, aryl, heteroaryl and trifluoromethyl groups, and the like.

Hence in an embodiment of the process provided herein, compound (4) is activated into compound (3'), wherein compound (3') is defined as compound (3) wherein LG represents the triflate group. The activation of compound (4) into compound (3') is a triflation reaction:

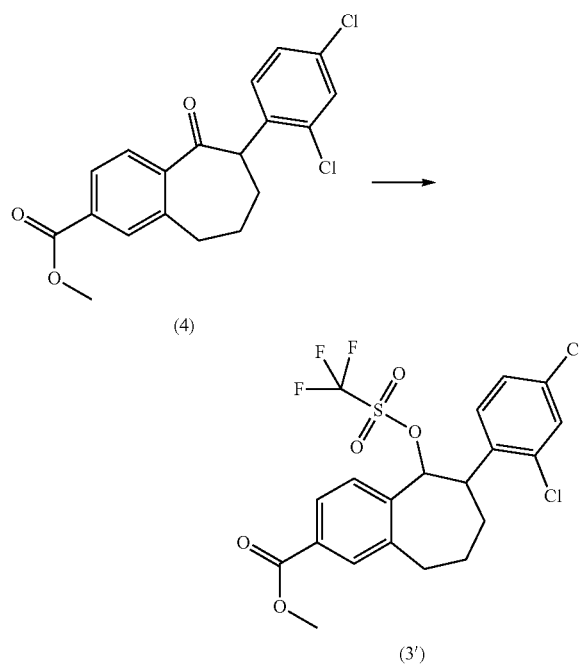

In such a reaction a triflation reagent is used, such as N-phenylbistriflimide or triflic anhydride.

Advantageously, N-phenylbistriflimide, also known as N,N-bis(trifluoromethylsulfonyl)aniline, is used as the triflation reagent. This reagent is advantageously used in a slight excess amount relative to compound (4), such as about 1.3 eq. (equivalent).

Suitable triflation media depend on the triflation reagent used, as known to one of skill in the Art.

The triflation reaction is carried out is an appropriate organic solvent, for example THF (tetrahydrofuran), Me-THF (methyl-tetrahydrofuran), acetonitrile, dioxane, or a mixture of toluene with Me-THF. Advantageously, Me-THF is used as organic solvent.

The triflation reaction is advantageously carried out with N-phenylbistriflimide as triflation reagent, in Me-THF as organic solvent. The temperature for the triflation reaction is advantageously chosen between 0° C. and room temperature.

The triflation reaction is carried out with a strong base, for example sodium hydride (NaH), potassium bis(trimethylsilyl)amide (KHMDS) or a phosphazene base such as BEMP (2-tert-butylimino-2-diethylamino-1,3-dimethylperhydro-1,3,2-diazaphosphorine) or BTPP (tert-butylimino-tri(pyrrolidino)phosphorane). Advantageously, sodium hydride is used as a strong base.

When NaH is used as strong base, the triflation reaction is carried out with a catalyst, for example DBU (1,8-diazabicyclo[5.4.0]undec-7-ene) or DBN (1,5-diazabicyclo(4.3.0)non-5-ene). Advantageously, DBU is used as catalyst.

Advantageously, the triflation reaction is carried out with sodium hydride as strong base, and with DBU as catalyst. Advantageously, a catalytic amount of DBU is used in the triflation reaction (such as about 0.2 eq.) and a stoichiometric amount of NaH (such as about 1.0-1.1 eq.), or a sub-stoichiometric amount of NaH (about 0.7-0.8 eq.) and a stoichiometric amount of DBU (about 1.0-1.2 eq.).

The triflation reaction is advantageously followed by a crystallization of the product obtained, according to crystallization techniques known to one of skill, so as to obtain compound (3) in a high purity, such as a purity level equal to or greater than 99%, before having it undergo the next steps of the process. Such a crystallization step may be carried out for example in acetonitrile, tert-amyl alcohol, heptane or diisopropylether. Advantageously, the crystallization is carried out in acetonitrile. The crystallization in acetonitrile is advantageously carried out at 0° C. and may be followed by drying at about 45° C.

In an embodiment of the process provided herein, the alpha-arylation of compound (5) to produce compound (4) is carried out with 1-iodo-2,4-dichlorobenzene or with 1-bromo-2,4-dichlorobenzene, which are both commercially available reactants. Advantageously, 1-bromo-2,4-dichlorobenzene is used as alpha-arylation reactant.

This alpha-arylation step may be carried out in an organic solvent, in presence of a palladium derivative as catalyst, of an appropriate ligand for the alpha-arylation reaction, and of a mineral base.

Advantageously, the alpha-arylation step is carried out in xylene, toluene, butyl acetate, isopropyl acetate or THF as organic solvent, using palladium(II) acetate (Pd(OAc)$_2$) or tris(dibenzylideneacetone)dipalladium(0) (Pd$_2$dba$_3$) as catalyst, and Xantphos (4,5-bis(diphenylphosphino)-9,9-dimethylxanthene) as ligand. Alternatively, when Pd$_2$dba$_3$ is used as catalyst, DPEPhos (bis[(2-diphenylphosphino)phenyl] ether) may be used as ligand. Another possible palladium derivative for use in the alpha-arylation step is [1,1'-bis(di-tert-butylphosphino)ferrocene]dichloropalladium(II) (PdCl$_2$(dtbpf)). Advantageously, the alpha-arylation step is carried out in toluene as organic solvent and with Pd$_2$dba$_3$ as catalyst. Under these conditions, heating at reflux may be applied.

Advantageously, the alpha-arylation step is carried out in the presence of a mineral base, such as K$_2$CO$_3$, K$_3$PO$_4$, Cs$_2$CO$_3$ and tBuONa. The mineral base is advantageously present in excess, such as 1.5 to 4 equivalent (eq.), more particularly 2.5 to 4 eq., in respect to the compound (5).

In the process provided herein, the Suzuki reaction applied on compound (3) to produce compound (2) is defined as a coupling reaction using an organoboron reagent and a transition metal-based catalyst, advantageously a palladium-based catalyst.

Advantageously, the organoboron reagent for use in the Suzuki coupling step of the process provided herein is reagent (1), namely (3S)-1-(3-fluoropropyl)-3-[4-(4,4,5,5-tetramethyl-1,3,2-dioxaborolan-2-yl)phenoxy]pyrrolidine, which is described in the patent application WO 2017/140669, or the corresponding acid (named reagent (2) as illustrated below), obtained by hydrolysis of the ester moiety of reagent (1), or a salt thereof such as the trifluoroborate potassium salt (named reagent (3) as illustrated below), obtained by salification of the boronic acid or ester moiety of reagent (2) or (1) by potassium hydrogen difluoride (KHF$_2$):

reagent (1)

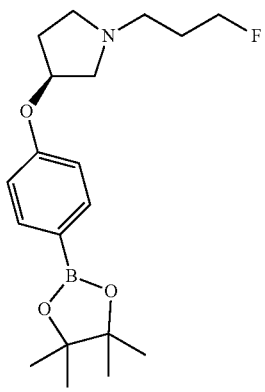

reagent (2)

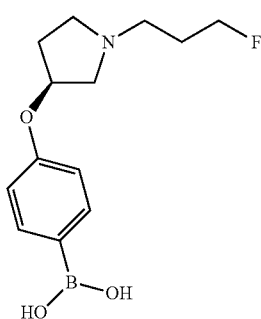

reagent (3)

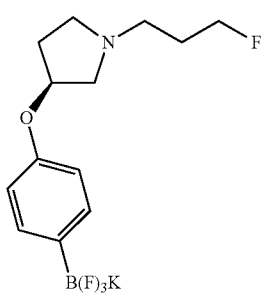

The content of patent application WO 2017/140669 for the preparation of (3S)-1-(3-fluoropropyl)-3-[4-(4,4,5,5-tetramethyl-1,3,2-dioxaborolan-2-yl)phenoxy]pyrrolidine (reagent (1)) is herein incorporated by reference.

The organoboron reagent for use in the Suzuki coupling step of the process provided herein is advantageously used in an equimolar amount (i.e. about 1 eq.) relative to the compound (3).

The palladium-based catalyst for use in the Suzuki coupling step of the process provided herein is advantageously the palladium complex bis(triphenylphosphine)palladium (II) dichloride, of formula $PdCl_2(PPh_3)_2$.

It is used in catalytic amount, for example at an amount of about 0.05 eq.

Suitable reaction media for the Suzuki coupling step of the process provided herein depend on the specific reagents used, as known to one of skill in the Art.

When bis(triphenylphosphine)palladium(II) dichloride is used as a catalyst, the reaction is advantageously carried out with an inorganic base, such as cesium carbonate ($Cs_2CO_3$), and in an organic solvent, such as a water/acetonitrile ($CH_3CN$) mixture.

In an embodiment of the process provided herein, a salification reaction may be performed after the Suzuki coupling step so as to obtain compound (2) in a salt form, advantageously in the form of an oxalate salt.

The Suzuki coupling step may thus be followed by a salification reaction, for example for obtaining an oxalate salt of compound (2) or a dibenzoyltartrate salt of compound (2).

The oxalate salt of compound (2) may be obtained using oxalic acid in a solvent selected from an ester-type solvent, such as an acetate solvent (for example ethyl acetate or isopropyl acetate), an ether-type solvent, such as MTBE (methyl-tertbutyl ether) or diisopropyl ether, and toluene.

Advantageously, the oxalate salt of compound (2) is obtained using oxalic acid in isopropylacetate, under heating (for example at about 70° C.).

The dibenzoyltartrate salt of compound (2) may be obtained using dibenzoyl tartaric acid (also named (2R,3R)-2,3-dibenzoyloxybutanedioic acid), in toluene and heptane.

The term "salification" of compound (2) as described above refers to the formation of a salt, allowing to precipitate compound (2).

Especially for the oxalate salt, such salification step allows to recover compound (2) from the reaction mixture in high purity. It also allows avoiding the use of a column chromatography for recovering the compound (2) from the reaction mixture in high purity.

Such a route of synthesis with a salt formation is particularly convenient for the industrial scale and for the storage of compound (2).

The dibenzoyl tartrate salt of compound (2) precipitates with a purity of about 93%, and the oxalate salt of compound (2) with a purity level equal to or greater than 98%.

The present text also describes compound (2) in the form of an oxalate salt:

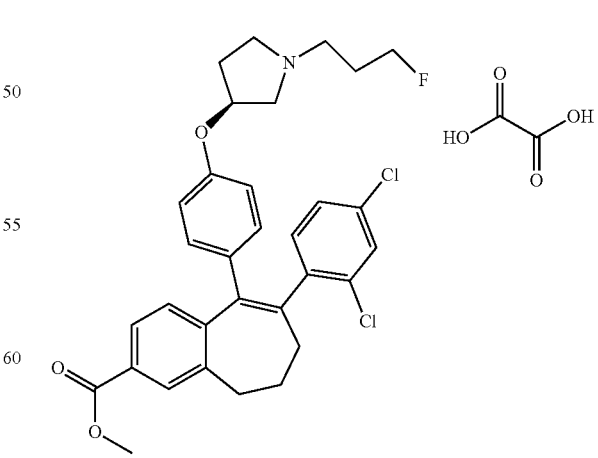

The present text also describes compound (2) in the form of a dibenzoyl tartrate salt:

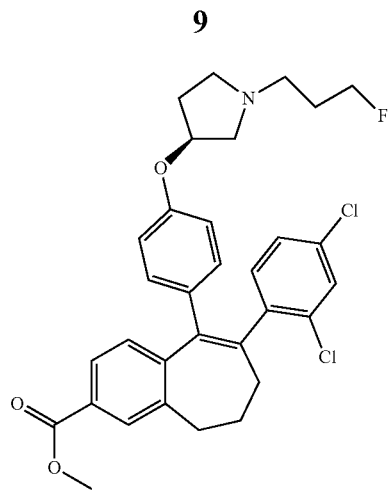
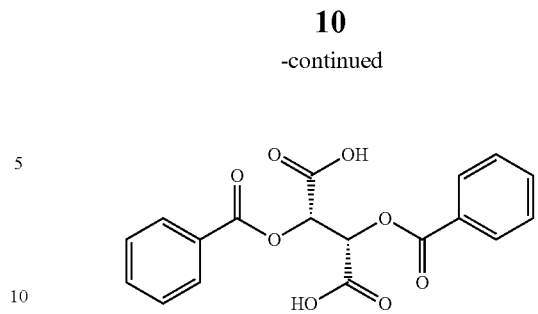
In view of the above description, an embodiment of the process provided herein for the preparation of compound (2) is represented in scheme 1 below, wherein LG' and LG are as defined above:
Scheme 1
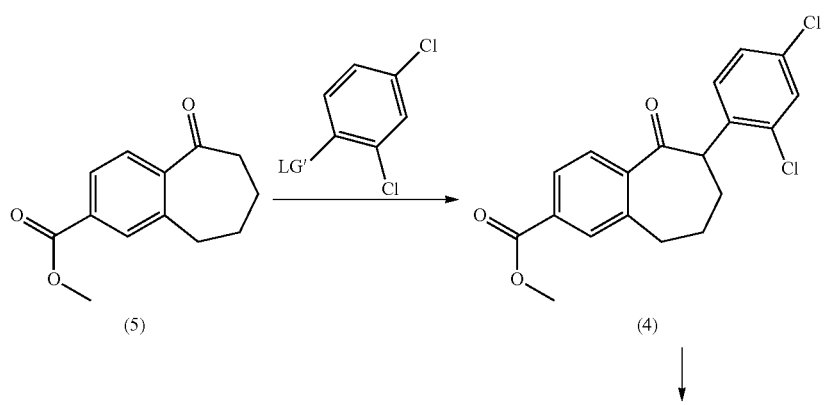
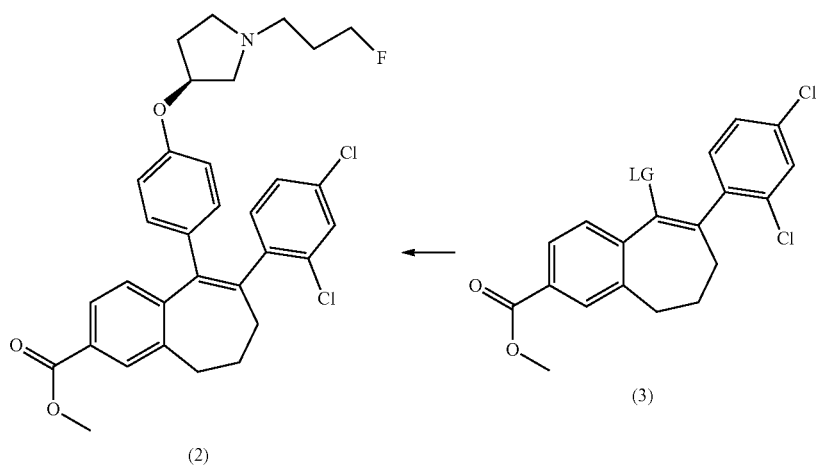

Another embodiment of the process provided herein for the preparation of compound (2) is represented in scheme 2 below, wherein LG' is as defined above:

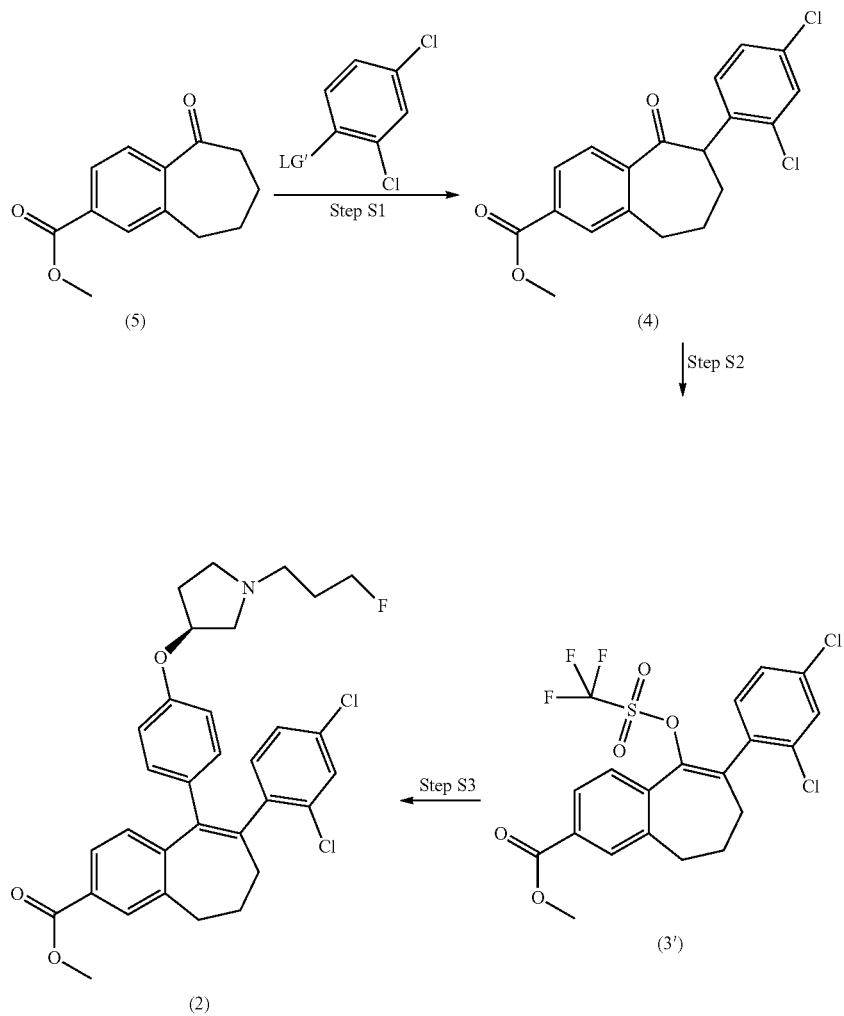

Compound (2) may undergo a saponification reaction, whereby the hydrolysis of the ester function will yield compound (1), bearing the corresponding acidic function. Such a saponification reaction may be carried out under conditions known to one of skill in the Art, namely in basic medium, advantageously using sodium hydroxide as a base, and in an organic solvent, advantageously an alcoholic solvent, such as methanol. Heating is applied during the saponification reaction so as to accelerate the hydrolysis of the ester moiety, for example at about 60° C. Such a saponification reaction is described in the patent application WO 2017/140669.

When a salt form of compound (2) is used, a free base of compound (2) is prepared before carrying out the saponification reaction, for example using an aqueous solution of potassium carbonate.

Provided herein is also a process for the preparation of compound (1) or a pharmaceutically acceptable salt thereof:

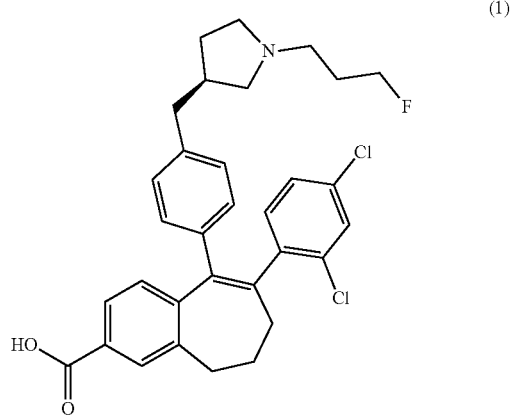 [SMILES: O=C(O)c1ccc2c(c1)CCCC(c1ccc(Cl)cc1Cl)=C2c1ccc(C[C@H]2CCN(CCCF)C2)cc1]

by saponification of compound (2):

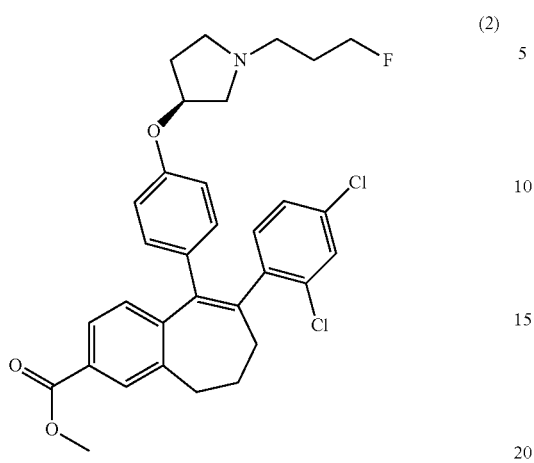

wherein compound (2) is obtained by the process described above.

Provided herein are also compounds (4), (3) and (3'), wherein LG represents a leaving group as described above:

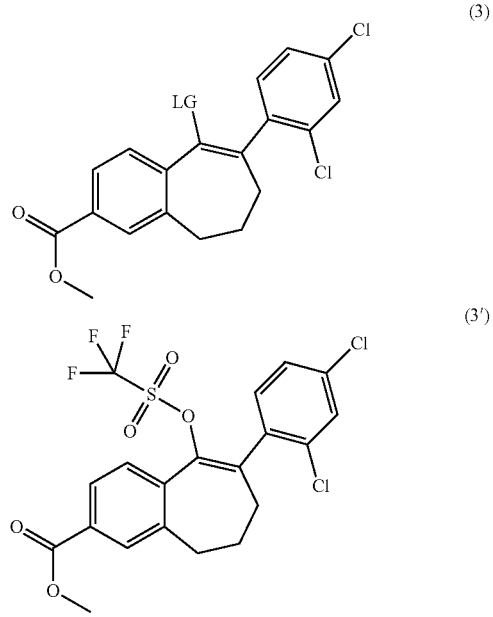

Compounds (4), (3) and (3') are useful as novel intermediates in the preparation of compound (2).

The process for the preparation of compound (2) provided herein is particularly advantageous for industrial implementation as it comprises fewer reaction steps than other processes of synthesis of compound (2) known to date, which are described in the patent application WO 2017/140669.

Scheme 3 below illustrates the shortest process for the synthesis of compound (2) described in WO 2017/140669. In scheme 3, each intermediate is designated under the same name as provided in said international patent application. This process as illustrated in scheme 3, starting from the commercially available intermediate 2-methoxy-6,7,8,9-tetrahydro-5H-benzo[7]annulen-5-one, is hereafter designated as "route A".

Scheme 3: Route A

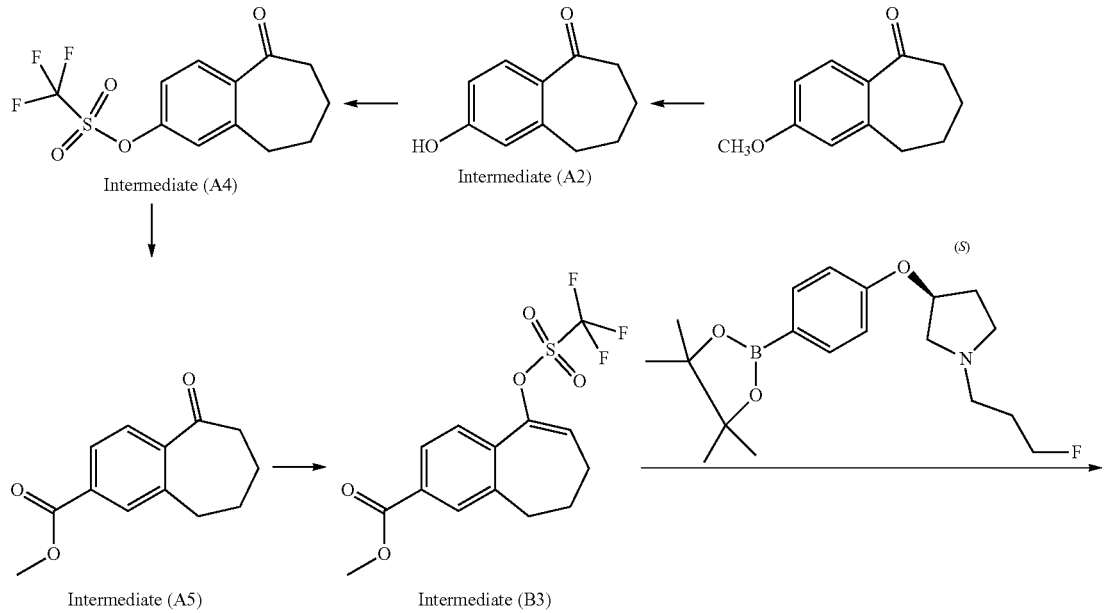

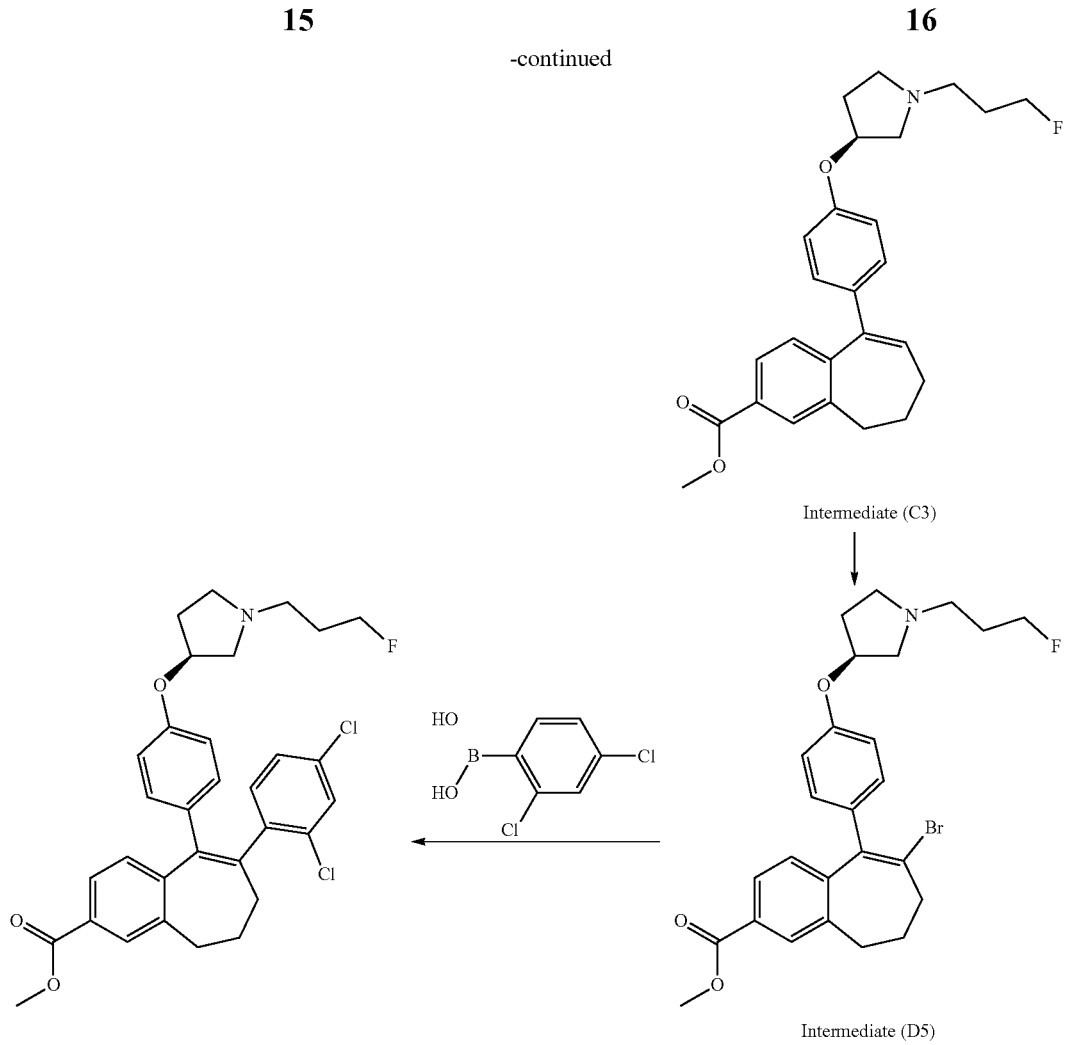

Intermediate (C3)

Intermediate (D5)

Under route A illustrated in scheme 3, compound (2) is obtained in 4 steps starting from methyl 5-oxo-6,7,8,9-tetrahydro-5H-benzo[7]annulene-2-carboxylate (same compound designated as "compound (5)" herein and as "intermediate (A5)" in WO 2017/140669). The process for the preparation of compound (2) provided herein therefore allows to obtain this compound in only 3 steps starting from methyl 5-oxo-6,7,8,9-tetrahydro-5H-benzo[7]annulene-2-carboxylate, compared to route A.

A second process of synthesis of compound (2) is described in WO 2017/140669, starting from the same intermediates 2-methoxy-6,7,8,9-tetrahydro-5H-benzo[7]annulen-5-one and intermediate (A2) as in scheme 3 above. This second process of synthesis of compound (2) is illustrated in scheme 4 below, wherein each intermediate is designated under the same name as provided in patent application WO 2017/140669. This process under scheme 4 is hereafter designated as "route B".

Scheme 4: Route B

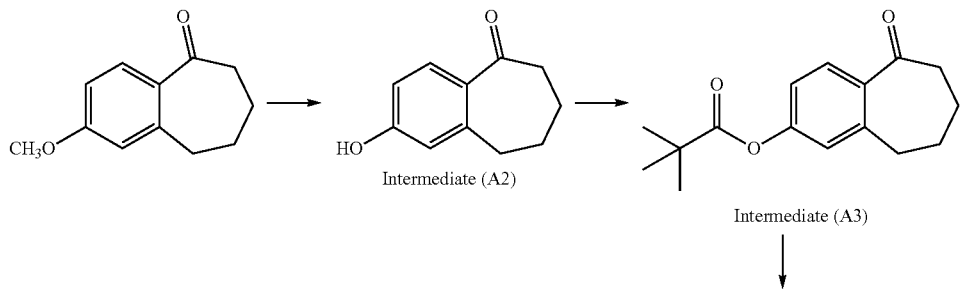

Intermediate (A2)

Intermediate (A3)

-continued

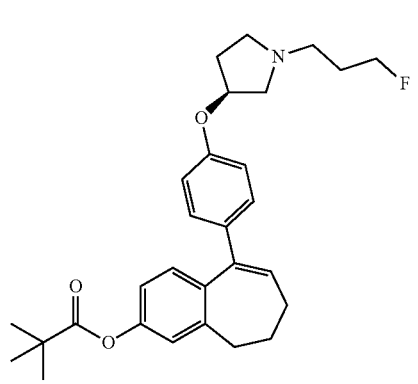

Intermediate (C2)

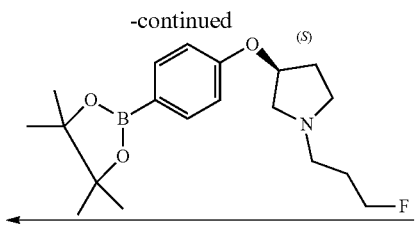

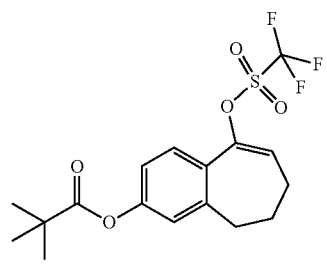

Intermediate (B2)

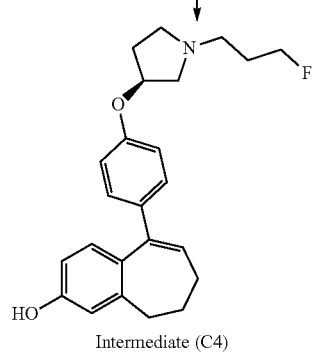

Intermediate (C4)

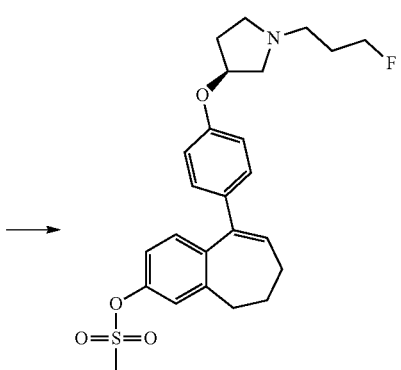

Intermediate (C5)

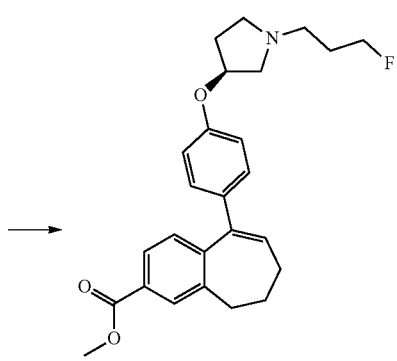

Intermediate (C3)

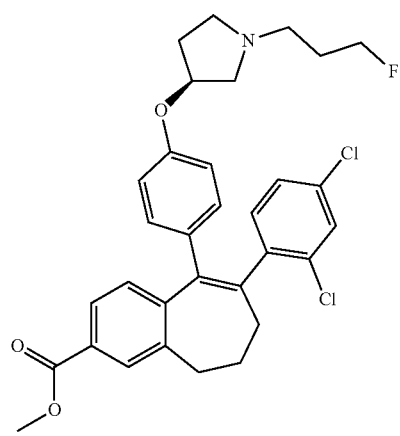

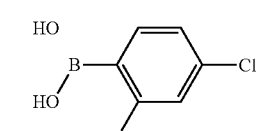

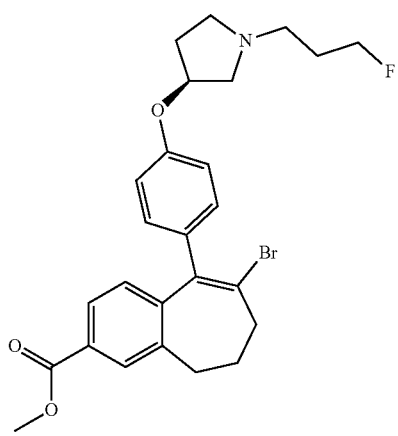

Intermediate (D5)

It therefore appears that the process for the preparation of compound (2) under scheme 4 entails many more reaction steps than the one under scheme 3.

Hence the new process for the synthesis of compound (2) as provided herein is shorter in terms of number of steps compared to both routes A and B as described in WO 2017/140669.

Below are described examples of protocols for the synthesis of compound (2), according to the new process of synthesis provided herein.

EXAMPLE 1: PREPARATION OF THE ORGANOBORON DERIVATIVE "REAGENT (1)"

The preparation of reagent (1), useful in the Suzuki coupling step of the process for synthesis of compound (2) as provided herein, is illustrated in scheme 5 below, reproduced from the patent application WO 2017/140669.

SCHEME 5

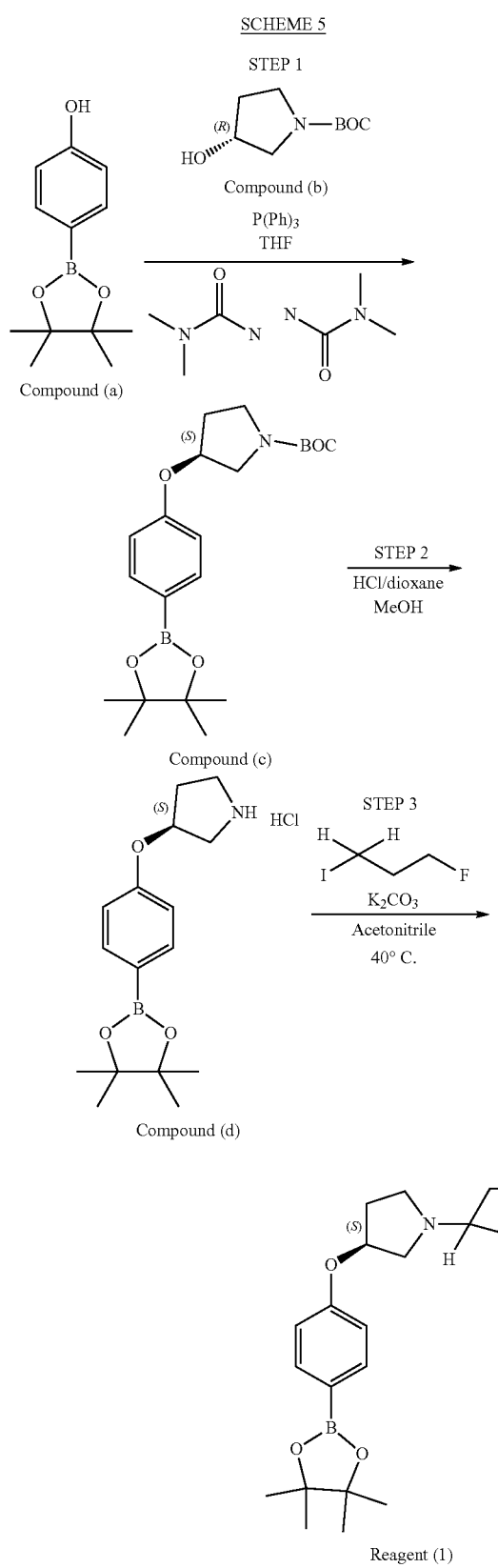

According to scheme 5, the commercially available compound (a) (4-(4,4,5,5-tetramethyl-1,3,2-dioxaborolan-2-yl)phenol) is condensed in tetrahydrofuran (THF) at room temperature on (R)-1-N-Boc-3-hydroxypyrrolidine, using N,N,N',N'-tetramethylazodicarboxamide as coupling agent.

According to step 2, the compound (c) thus obtained is N-deprotected in methanol (MeOH) at room temperature using an acidic agent, for example a solution of HCl 4N in dioxane.

Alkylation of the pyrrolidine nitrogen is then performed under step 3 by reacting compound (d) with the corresponding 1,1-disubstituted 1-halogeno-3-fluoro propane, for example 1-iodo-3-fluoropropane, in acetonitrile in presence of potassium carbonate ($K_2CO_3$) at about 40° C.

Steps 1 to 3 of scheme 5 are illustrated by the detailed protocols below.

The $^1$H NMR spectra were performed on a BrukerAvance DRX-400 spectrometer, with the chemical shifts (δ in ppm) in the solvent dimethyl sulfoxide-d6 (dDMSO-d6) referenced at 2.50 ppm at a temperature of 303 K. Coupling constants (J) are given in Hertz.

The liquid chromatography/mass spectrography (LC/MS) data were obtained on a UPLC Acquity Waters instrument, light scattering detector Sedere and SQD Waters mass spectrometer using UV detection DAD 210<l<400 nm and column Acquity UPLC CSH C18 1.7 μm, dimension 2.1×30 mm, mobile phase $H_2O$+0.1% $HCO_2H$/$CH_3CN$+0.1% $HCO_2H$.

Compound (c). Tert-butyl (3S)-3-[4-(4,4,5,5-tetramethyl-1,3,2-dioxaborolan-2yl)phenoxy]pyrrolidine-1-carboxylate

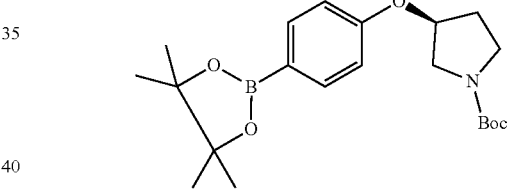

To a solution of 4-(4,4,5,5-tetramethyl-1,3,2-dioxaborolan-2-yl)phenol (a) (82.7 g, 364.51 mmol) in THF (2 L) was added under argon (R)-1-N-Boc-3-hydroxypyrrolidine (b) (84.43 g, 437.41 mmol) followed by N,N,N',N'-tetramethylazodicarboxamide (99.1 g, 546.77 mmol). The clear reaction mixture turned orange and triphenylphosphine (143.41 g, 546.77 mmol) was added. The reaction mixture was stirred at room temperature for 24 hours, meanwhile a precipitate of triphenylphosphine oxide formed ($Ph_3P$=O). The reaction mixture was poured in water (1.5 L) and extracted with ethyl acetate (AcOEt) (3×1.5 L). Gathered organic phases were dried over magnesium sulfate ($MgSO_4$), filtered and concentrated under reduced pressure. The residue was taken up into diisopropylether (1.5 L) and the solid formed ($Ph_3P$=O) was filtered. The solvent was concentrated under reduced pressure and the residue purified by column chromatography eluting with a mixture of heptane with AcOEt (90/10; v/v) to give 145 g (100%) of tert-butyl (3S)-3-[4-(4,4,5,5-tetramethyl-1,3,2-dioxaborolan-2-yl)phenoxy]pyrrolidine-1-carboxylate (c) as a colorless oil.

$^1$H NMR (400 MHz, DMSO-d6, δ ppm): 1.27 (s, 12H); 1.39 (s, 9H); 2.05 (m, 1H); 2.14 (m, 1H); 3.37 (3H); 3.55 (m, 1H); 5.05 (s, 1H); 6.94 (d, J=8.4 Hz, 2H); 7.61 (d, J=8.4 Hz, 2H).

Compound (d). (3S)-3-[4-(4,4,5,5-tetramethyl-1,3,2-dioxaborolan-2yl)phenoxy]pyrrolidine, hydrochloride

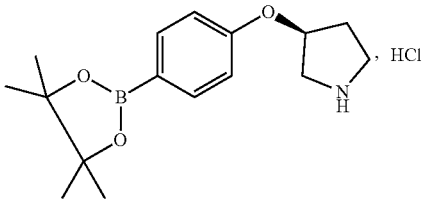 [SMILES: CC1(C)OB(c2ccc(O[C@H]3CCNC3)cc2)OC1(C)C ; "HCl"]

To a solution of (S)-tert-butyl 3-(4-(4,4,5,5-tetramethyl-1,3,2-dioxaborolan-2-yl)phenoxy)pyrrolidine-1-carboxylate (c) (80 g, 195.23 mmol) in MeOH (450 ml) was added slowly HCl 4N in dioxane (250 ml).

After 1.5 hours, the reaction mixture was concentrated under reduced pressure and the residue was taken up into Et$_2$O with stirring to give a solid which then was filtered and dried under vacuum to give compound (d) 61.8 g (95%) as a white powder.

$^1$H NMR (400 MHz, DMSO-d6, δ ppm): 1.28 (s: 12H); 2.10 (m: 1H); 2.21 (m: 1H); 3.31 (3H); 3.48 (m: 1H); 5.19 (m: 1H); 6.97 (d, J=8.4 Hz: 2H); 7.63 (d, J=8.4 Hz: 2H); 9.48 (s: 1H); 9.71 (s: 1H).

LC/MS (m/z, MH$^+$): 290

Reagent (1). (3S)-1-(3-fluoropropyl)-3-[4-(4,4,5,5-tetramethyl-1,3,2-dioxaborolan-2-yl)phenoxy]pyrrolidine

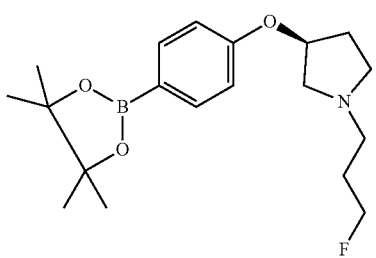 [SMILES: CC1(C)OB(c2ccc(O[C@H]3CCN(CCCF)C3)cc2)OC1(C)C]

To a suspension of (S)-3-(4-(4,4,5,5-tetramethyl-1,3,2-dioxaborolan-2-yl)phenoxy)pyrrolidine hydrochloride (d) (20 g, 61.42 mmol) in acetonitrile (100 ml), was added K$_2$CO$_3$ (21.22 g, 153.54 mmol) and 1-iodo-3-fluoropropane (12.15 g, 61.42 mmol), under argon. The reaction mixture was stirred at 40° C. for 24 hours. After cooling to room temperature, the reaction mixture was filtered and washed with acetonitrile. The filtrate was concentrated under reduced pressure and the residue was taken up in DCM and the solid formed was filtered and washed with DCM. The filtrate was concentrated to give reagent (1) 21.5 g (100%) as a yellow foam.

$^1$H NMR (400 MHz, DMSO-d6, δ ppm): 1.27 (s, 12H); 1.77 (m, 2H); 1.84 (m, 1H); 2.27 (m, 1H); 2.41 (m, 1H); 2.49 (2H); 2.62 (dd, J=2.6 and 10.4 Hz, 1H); 2.69 (m, 1H); 2.83 (dd, J=6.2 and 1.4 Hz, 1H); 4.47 (td, J=6.2 and 47 Hz, 2H); 4.99 (m, 1H); 6.77 (d, J=8.4 Hz, 2H); 7.58 (d, J=8.4 Hz, 2H).

LC/MS (m/z, MH$^+$): 350

EXAMPLE 2: SYNTHESIS OF COMPOUND (2) FROM CARBOXYMETHOXYBENZOSUBERONE (5)

The numbering of the intermediate and final compounds (2), (3'), (4) and (5) refer to scheme 2 described before.

In the first step S1, the 5-oxo-6,7,8,9-tetrahydrobenzo[7]annulene core of compound (5) (carboxymethoxybenzosuberone) is arylated at the 6-position via a palladium catalyzed coupling of 1-bromo-2,4-dichloro-benzene in refluxing toluene and in the presence of potassium carbonate, to yield the 2,4-dichlorophenyl precursor (4) isolated as a Me-THF solution after silica gel filtration.

In the second step S2, the crude Me-THF solution of compound (4) is reacted with N-phenyl-bis-triflimide in the presence of catalytic DBU and an excess of sodium hydride. After water washing and solvent exchange to acetonitrile, the desired triflated compound (3') is isolated by crystallization as a white solid.

In a third step S3, the cyclic enol triflate (3') is coupled to the chiral boronic ester "reagent (1)" as described earlier via a palladium catalyzed Suzuki reaction performed in an acetonitrile/water mixture at 40±3° C., using cesium carbonate as a base. After aqueous work-up and solvent exchange with isopropylacetate, residual palladium is eliminated by sequential ethylenediamine, charcoal and dimercaptotriazine grafted silica treatments. The crude oxalate salt of compound (2) is isolated by crystallization in isopropylacetate.

These steps are illustrated by the detailed protocols below.

The $^1$H NMR spectra were performed on a 300 or 400 MHz Bruker Avance spectrometer, with the chemical shifts (δ in ppm) in the solvent dimethyl sulfoxide-d6 (dDMSO-d6) referenced at 2.50 ppm at a temperature of 303 K. Coupling constants (J) are given in Hertz.

The liquid chromatography/mass spectrography (LC/MS) data were obtained on a UPLC-SQD Waters instrument, evaporating light scattering detector Sedere and SQD Waters mass spectrometer using UV detection DAD 210<<400 nm and column Acquity UPLC CSH C18 1.7 μm, dimension 2.1×50 mm, mobile phase H$_2$O+0.1% HCO$_2$H/CH$_3$CN+ 0.1% HCO$_2$H.

2.1: Steps S1 and S2 Concatenated

A degassed mixture of methyl 5-oxo-6,7,8,9-tetrahydro-5H-benzo[7]annulene-2-carboxylate (5) (40 g), potassium carbonate (K$_2$CO$_3$, 40 to 101 g i.e. 1.5 to 4 eq.), bromo-dichlorobenzene (62.1 g), Xantphos (21.2 g) and Pd$_2$dba$_3$ (8.39 g) is refluxed in toluene (320 ml) under nitrogen and vigorous stirring until completion.

After cooling to room temperature, insoluble material is eliminated by filtration on a pad of silica (80 g), followed by washings of the filter with toluene (600 ml). Toluene is distilled off from the filtrate and exchanged with Me-THF to yield a solution of the α-arylation product (4) (methyl 6-(2,4-dichlorophenyl)-5-oxo-6,7,8,9-tetrahydrobenzo[7]annulene-2-carboxylate) in MeTHF (400 ml), used as is in the next step.

A sample of pure product (4) has been isolated by silica gel chromatography of an aliquot (eluent: dichloromethane-heptane).

$^1$H NMR (400 MHz, DMSO-d6 in ppm) of the isolated compound (4): 1.77 (m, 1H) 2.00 (m, 1H); 2.18 (m, 2H); 3.08 (m, 1H); 3.20 (m, 1H); 3.89 (s, 3H); 4.46 (dd, J=11.3, 3.7 Hz, 1H); 7.46 (m, 2H); 7.59 (d, J=2.0 Hz, 1H); 7.64 (d, J=7.9 Hz, 1H); 7.91 (dd, J=8.0, 1.4 Hz, 1H); 7.94 (s, 1H).

LC/MS ([M+H]$^+$): 363

To the Me-THF solution of compound (4) obtained in step S1 (scale: 40 g of compound (4)) is added N,N-bis(trifluoromethylsulfonyl)aniline (80 g). The resulting solution is added dropwise at 0° C., under stirring, to a Me-THF (200 ml) suspension of NaH (10 g-60% dispersion in oil) containing DBU (5 ml). The reaction mixture is stirred at room temperature until completion.

After cooling to 0° C., acetic acid (4 ml), followed by water (400 ml), are added dropwise. The aqueous phase is separated at room temperature and the organic phase is washed with diluted aqueous sodium chloride (NaCl, 0.6 M; 3×400 ml). Me-THF is distilled off and exchanged with acetonitrile. After elimination of insoluble material by filtration in hot acetonitrile, compound (3') (methyl 6-(2,4-dichlorophenyl)-5-(trifluoromethylsulfonyloxy)-8,9-dihydro-7H-benzo[7]annulene-2-carboxylate) is crystallized in 250 ml of acetonitrile, isolated by filtration and washings with cold acetonitrile and heptane, to yield 61.2 g of pure triflate as a white solid.

Yield: 67.4% (in 2 steps S1 and S2).

$^1$H NMR (400 MHz, DMSO-d6 in ppm): 2.18 (m, 2H); 2.41 (m, 2H); 2.95 (m, 2H); 3.90 (s, 3H); 7.55 (m, 2H); 7.68 (d, J=8 Hz, 1H); 7.80 (d, J=1.8 Hz, 1H) 8.01 (m, 2H).

LC/MS (EI m/z): 494$^+$

Purity of compound (3'): 99.0%, measured by HPLC:

Mobile phase: water/acetonitrile/HCOOH;

Stationary phase: XSelect CSH C18—3.5 μm (Waters) or equivalent;

Column length: 100 mm;

Column internal diameter: 4.6 mm;

Flow rate: 1 mL/minute;

Injection volume: 10 μL;

Detection: 254 nm (UV).

2.2: Step S3

A degassed mixture of the triflate (3') (20 g), the boronic ester "reagent (1)" (14.1 g), Cs$_2$CO$_3$ (19.7 g), bis(triphenylphosphine) palladium(II)dichloride (1.4 g), water (100 ml) and acetonitrile (260 ml), is stirred at 40° C. under nitrogen. After complete conversion, the reaction medium is cooled to room temperature, isopropylacetate (100 ml) is added and the aqueous phase is separated. The organic phase is washed with diluted aqueous NaCl (0.3 M; 2×200 ml), dried by azeotropic distillation of isopropylacetate and treated subsequently with ethylenediamine, charcoal and dimercaptotriazine grafted silica, to remove residual palladium.

The resulting solution of compound (2), namely 6-(2,4-dichlorophenyl)-5-{4-[1-(3-fluoro-propyl)-pyrrolidin-3-yloxy]-phenyl}-8,9-dihydro-7H-benzocycloheptene-2-carboxylic acid methyl ester, in isopropylacetate, adjusted at 200 ml, is heated to 70° C. and an oxalic acid (3.6 g) solution in isopropylacetate (43 ml) is added dropwise under stirring. After seeding (using seeds previously prepared on another batch of product by conventional crystallisation techniques) and cooling to 0° C., the desired oxalate salt of compound (2), depicted below, crystallizes and is isolated by filtration in a 70% yield (18.6 g, white powder):

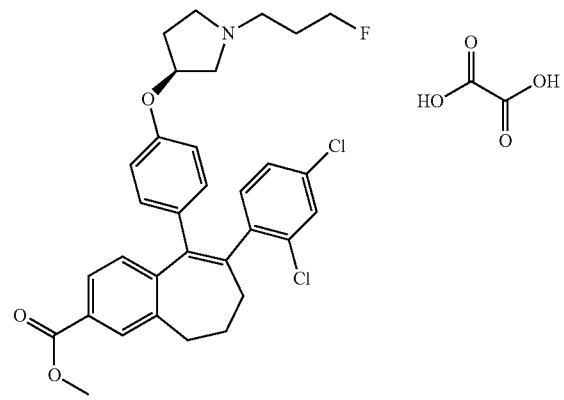 [SMILES: COC(=O)c1ccc2c(c1)CCCC(c1ccc(Cl)cc1Cl)=C2c1ccc(O[C@H]2CCN(CCCF)C2)cc1 ; O=C(O)C(=O)O]

$^1$H NMR (400 MHz, DMSO-d6 in ppm): 7.92 (d, J=2.0 Hz, 1H); 7.78 (dd, J=8.0 and 2.0 Hz, 1H); 7.59 (d, J=2.2 Hz, 1H); 7.29 (dd, J=8.3 and 2.2 Hz, 1H); 7.22 (d, J=8.3 Hz, 1H); 6.90 (d, J=8.0 Hz, 1H); 6.78 (d, J=9.0 Hz, 2H); 6.73 (d, J=9.0 Hz, 2H); 4.98 (m, 1H); 4.50 (dt, J=47.2 and 5.7 Hz, 2H); 3.86 (s, 3H); 3.49 (dd, J=12.8 and 5.8 Hz, 1H); from 3.38 to 3.08 (m, 5H); 2.94 (t, J=5.0 Hz, 2H); 2.34 (m, 1H); from 2.23 to 2.11 (m, 3H); from 2.07 to 1.93 (m, 2H).

LC/MS ([M+H]$^+$): 568

Purity of compound (2), oxalate salt: 98.2%, measured by HPLC under the same conditions as described in step S2 above.

EXAMPLE 3: ALTERNATIVE PROTOCOLS FOR STEP S1

3.1: Alternative 1

A 2 M THF solution of sodium tert-butoxide (19.48 ml) is added dropwise at 60° C. to a degassed mixture containing compound (5) (5 g), 1-bromo-2,4-dichlorobenzene (7.76 g), palladium acetate (257 mg), Xantphos (660 mg) and THF (20 ml). The reaction is heated at 60° C. until completion, cooled to room temperature, quenched with molar aqueous KH$_2$PO$_4$. After ethyl acetate extraction, water washings and purification by silica gel chromatography, compound (4) is isolated in a 70% yield and 92% purity.

$^1$H NMR (400 MHz, DMSO-d6 in ppm): 1.78 (m, 1H); 2.01 (m, 1H); 2.19 (m, 2H); 3.10 (m, 1H); 3.22 (m, 1H); 3.89 (s, 3H); 4.47 (dd, J=11.3, 3.6 Hz, 1H); 7.47 (m, 2H); 7.61 (d, J=1.8 Hz, 1H); 7.65 (d, J=7.9 Hz, 1H); 7.92 (d, J=7.7 Hz, 1H); 7.95 (s, 1H).

LC/MS ([M+H]$^+$): 363

3.2: Alternative 2

A degassed mixture containing compound (5) (0.5 g), 1-iodo-2,4-dichlorobenzene (0.76 ml), toluene (9 ml), water (1 ml), Cs$_2$CO$_3$ (1.05 g), palladium acetate (50 mg) and Xantphos (250 mg) is heated to reflux during about 22 hours. After cooling to room temperature, the organic phase is diluted with dichloromethane, washed with water and purified by chromatography on silica gel to yield 730 mg (87%) of a white solid.

$^1$H NMR (400 MHz, DMSO-d6 in ppm): 1.78 (m, 1H); 2.01 (m, 1H); 2.19 (m, 2H); 3.09 (m, 1H); 3.21 (m, 1H); 3.89 (s, 3H); 4.47 (dd, J=11.3, 3.7 Hz, 1H); 7.47 (m, 2H); 7.60 (d, J=2.0 Hz, 1H); 7.64 (d, J=8.1 Hz, 1H); 7.92 (dd, J=7.9, 1.5 Hz, 1H); 7.95 (s, 1H).

EXAMPLE 4: ALTERNATIVE PROTOCOLS FOR STEP S2

3.1: Alternative 1

A 0.5 M THF solution of potassium bis-trimethylsilylamide (7.70 ml) is added dropwise at −50° C. to a mixture of compound (4) (1 g) and N-phenylbis-triflimide (1.22 g) in THF (18 ml). After warming up to room temperature, the reaction medium is quenched with water at 0-5° C., extracted with dichloromethane followed by ethyl acetate, and purified by silica gel chromatography (eluent: dichloromethane-heptane) to afford the desired compound (3') in an 80% yield and 90% purity measured by LC/MS.

$^1$H NMR (400 MHz, DMSO-d6 in ppm): 2.18 (m, 2H); 2.41 (m, 2H); 2.95 (m, 2H); 3.89 (s, 3H); 7.55 (m, 2H); 7.68 (d, J=8.1 Hz, 1H); 7.80 (d, J=1.7 Hz, 1H); 8.01 (m, 2H).

LC/MS ([M+H]$^+$): 494

3.2: Alternative 2

DBU (247 μl) is added dropwise at 0-5° C. to a suspension containing compound (4) (500 mg), and N,N-bis(trifluoromethylsulfonyl)aniline (639 mg) in acetonitrile (2 ml). The conversion rate is about 80% after stirring 22 hours at room temperature. The reaction mixture is cooled down to 0-5° C. and sodium hydride (27.5 mg of a 60% dispersion in oil) is added. After 1.5 hours stirring at room temperature, the conversion rate is about 100%. The resulting suspension is cooled down to 0-5° C., filtrated and washed with pre-cooled acetonitrile (0.5 ml) followed by water (2 ml) to yield 460 mg of compound (3') as a white powder (yield: 67.5%) with a purity of 98% measured by LC/MS.

$^1$H NMR (400 MHz, DMSO-d6 in ppm): 2.18 (m, 2H); 2.42 (m, 2H); 2.95 (m, 2H); 3.90 (s, 3H); 7.55 (m, 2H); 7.68 (d, J=7.9 Hz, 1H); 7.82 (s, 1H); 8.02 (m, 2H).

As shown in the above examples, the new process of synthesis for compound (2) provided herein allows a global yield, from compound (5) to compound (2), of about 33 to 49%. This is a greater yield than the one found in the previously described process of synthesis as set forth in scheme 3, wherein the yield for obtaining compound (2) is about 26% when starting from the same compound methyl 5-oxo-6,7,8,9-tetrahydro-5H-benzo[7]annulene-2-carboxylate.

Also, the new process of synthesis provided herein allows to obtain compound (2) in a good yield without the need to perform column chromatographies after the Suzuki coupling step, which was needed in the syntheses routes previously known, but which is not appropriate when seeking a synthesis route applicable at the industrial level.

The invention claimed is:

1. A process for the preparation of compound (2):

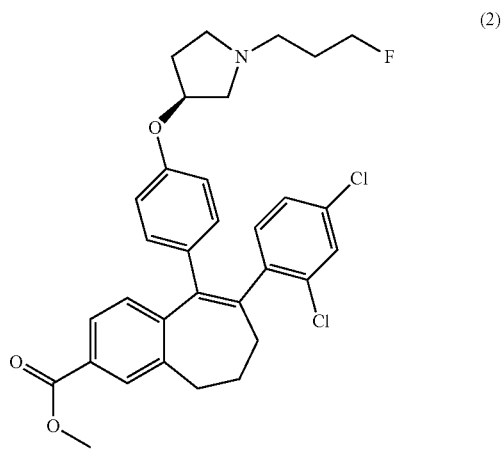 [SMILES: COC(=O)c1ccc2c(c1)CCCC(c1ccc(Cl)cc1Cl)=C2c1ccc(O[C@H]2CCN(CCCF)C2)cc1]

in the base form or in a salt form, the process comprising a Suzuki coupling of compound (3),

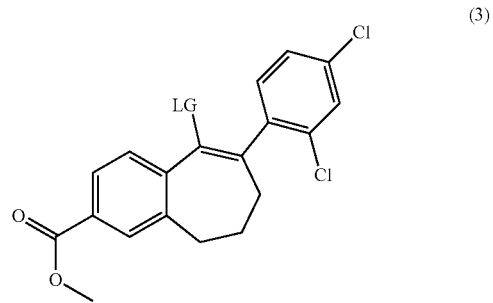

wherein LG represents a leaving group chosen from a triflate group and a nonaflate group, with an organoboron reagent OrganoB-X wherein OrganoB is a boron derivative and X is a (3S)-1-(3-fluoropropyl)-3-phenoxypyrrolidine moiety of the following formula:

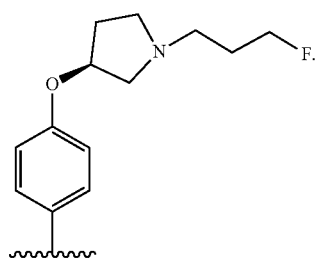 [SMILES: *c1ccc(O[C@H]2CCN(CCCF)C2)cc1]

2. The process according to claim 1, wherein the organoboron reagent is chosen from (3S)-1-(3-fluoropropyl)-3-[4-(4,4,5,5-tetramethyl-1,3,2-dioxaborolan-2-yl) phenoxy]pyrrolidine, the corresponding acid, and a salt thereof.

3. The process according to claim 2, wherein the organoboron reagent is chosen from reagents (1), (2), and (3):

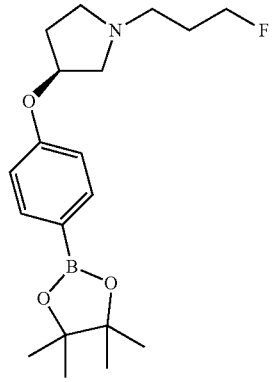

reagent (1)

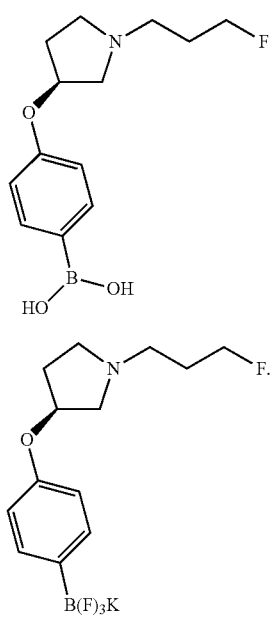

reagent (2)

reagent (3)

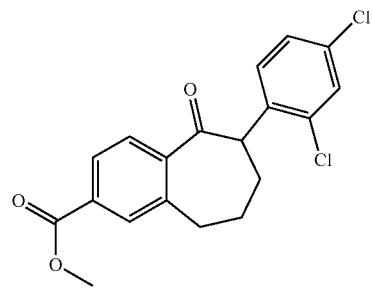

(4)

with a reagent bearing a leaving group chosen from a triflate group and a nonaflate group.

11. The process according to claim 10, wherein the leaving group on the reagent bearing a leaving group is a triflate group.

12. The process according to claim 11, wherein sodium hydride and DBU are used in the reaction of compound (4) with the reagent bearing a leaving group.

13. The process according to claim 11, wherein the reagent bearing a leaving group is N-phenylbistriflimide.

14. The process according to claim 10, wherein compound (4) is obtained by alpha-arylation of methyl 5-oxo-6,7,8,9-tetrahydro-5H-benzo[7]annulene-2-carboxylate with 1-LG'-2,4-dichlorobenzene, wherein LG' represents a leaving group.

15. The process according to claim 14, wherein the leaving group LG' is a halogen atom chosen from bromine and iodine.

16. The process according to claim 14, wherein the alpha-arylation is carried out in presence of a palladium derivative, a ligand, and a mineral base.

17. The process according to claim 16, wherein the palladium derivative is chosen from Pd(OAc)$_2$ and Pd$_2$dba$_3$.

18. The process according to claim 16, wherein the mineral base is chosen from K$_2$CO$_3$, K$_3$PO$_4$, Cs$_2$CO$_3$, and tBuONa.

19. The process according to claim 16, wherein the alpha-arylation is carried out in the presence of Pd$_2$dba$_3$ and 4,5-bis(diphenylphosphino)-9,9-dimethylxanthene.

20. A process for the preparation of compound (1) or a pharmaceutically acceptable salt thereof:

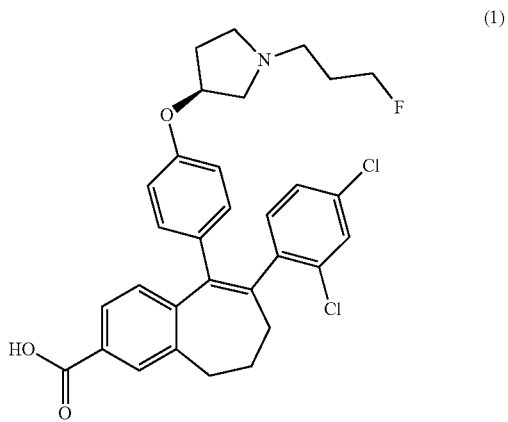 [SMILES: O=C(O)c1ccc2c(c1)CCCC(c1ccc(Cl)cc1Cl)=C2c1ccc(O[C@H]2CCN(CCCF)C2)cc1]

(1)

4. The process according to claim 1, wherein the Suzuki coupling is carried out in the presence of a palladium complex.

5. The process according to claim 4, wherein the palladium complex is bis(triphenylphosphine) palladium (II) dichloride.

6. The process according to claim 1, wherein the Suzuki coupling is carried out in the presence of bis(triphenylphosphine) palladium (II) dichloride and cesium carbonate.

7. The process according to claim 1, wherein the leaving group LG in compound (3) is a triflate group.

8. The process according to claim 1, further comprising a salification reaction performed after the Suzuki coupling.

9. The process according to claim 8, wherein compound (2) is prepared in the form of an oxalate salt, and wherein the oxalate salt of compound (2) is obtained using oxalic acid.

10. The process according to claim 1, wherein compound (3) is obtained by reacting compound (4):

by saponification of compound (2):

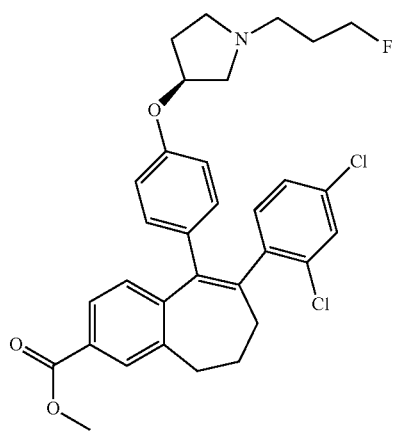

(2)

wherein compound (2) is prepared in the base form or in a salt form by a Suzuki coupling of compound (3),

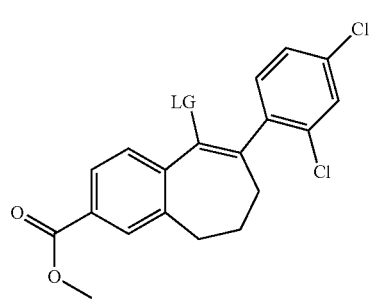

(3)

wherein LG represents a leaving group chosen from a triflate group and a nonaflate group, with an organoboron reagent OrganoB-X wherein OrganoB is a boron derivative and X is a (3S)-1-(3-fluoropropyl)-3-phenoxypyrrolidine moiety of the following formula:

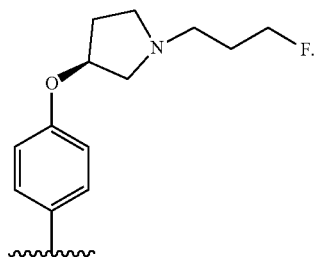 [SMILES: *c1ccc(O[C@H]2CCN(CCCF)C2)cc1]

21. The process according to claim 6, wherein the Suzuki coupling is carried out in an organic solvent.

22. The process according to claim 9, wherein the oxalate salt of compound (2) is obtained in isopropylacetate.

23. The process according to claim 13, wherein the reaction of compound (4) with a reagent bearing a leaving group is carried out in Me-THF.

24. The process according to claim 16, wherein the alpha-arylation is carried out in an organic solvent.

25. The process according to claim 19, wherein the alpha-arylation is carried out in toluene.

26. The process according to claim 8, wherein compound (2) is prepared in the form of a dibenzoyl tartrate salt by a salification reaction performed after the Suzuki coupling.

27. The process according to claim 26, wherein the dibenzoyl tartrate salt of compound (2) is obtained using dibenzoyl tartaric acid.

28. The process according to claim 20, further comprising a salification reaction performed after the Suzuki coupling.

\* \* \* \* \*

UNITED STATES PATENT AND TRADEMARK OFFICE
CERTIFICATE OF CORRECTION

PATENT NO. : 12,157,721 B2
APPLICATION NO. : 17/193706
DATED : December 3, 2024
INVENTOR(S) : Rabion et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 921 days.

Signed and Sealed this
Twentieth Day of May, 2025

Coke Morgan Stewart
*Acting Director of the United States Patent and Trademark Office*